(12) United States Patent
Lo Franco et al.

(10) Patent No.: US 10,226,498 B2
(45) Date of Patent: Mar. 12, 2019

(54) ANTIANGIOGENIC USE OF LIQUID PHYTOCOMPLEXES FROM OLIVE

(71) Applicant: FATTORIA LA VIALLA DI GIANNI, ANTONIO E BANDINO LO FRANCO—SOCIETA' AGRICOLA SEMPLICE, Arezzo (IT)

(72) Inventors: Gianni Lo Franco, Arezzo (IT); Adriana Albini, Sesto San Giovanni (IT); Massimo Pizzichini, Rome (IT); Teresa Rossi, Reggio Emilia (IT); Antonino Bruno, Milan (IT); Arianna Pagani, Pero (IT)

(73) Assignee: FATTORIA LA VIALLA DI GIANNI, ANTONIO E BANDIDO LO FRANCO —SOCIETA' AGRICOLA SEMPLICE, Arezzo (IT)

( * ) Notice: Subject to any disclaimer, the term of this patent is extended or adjusted under 35 U.S.C. 154(b) by 4 days.

(21) Appl. No.: 15/033,586

(22) PCT Filed: Oct. 31, 2014

(86) PCT No.: PCT/IB2014/065746
§ 371 (c)(1),
(2) Date: Apr. 29, 2016

(87) PCT Pub. No.: WO2015/063736
PCT Pub. Date: May 7, 2015

(65) Prior Publication Data
US 2016/0250272 A1 Sep. 1, 2016

(30) Foreign Application Priority Data
Oct. 31, 2013 (IT) .............................. MI2013A1814

(51) Int. Cl.
*A61K 36/00* (2006.01)
*A61K 36/63* (2006.01)
*A23L 2/52* (2006.01)
*A23L 33/10* (2016.01)
*A23L 33/105* (2016.01)
*A23L 33/16* (2016.01)
*A61K 9/00* (2006.01)
*A61K 31/05* (2006.01)
*A61K 31/351* (2006.01)
*A61K 31/7004* (2006.01)
*A61K 31/7034* (2006.01)
*A61K 31/7048* (2006.01)
*A61K 33/00* (2006.01)
*A61K 33/06* (2006.01)

(52) U.S. Cl.
CPC ............... *A61K 36/63* (2013.01); *A23L 2/52* (2013.01); *A23L 33/10* (2016.08); *A23L 33/105* (2016.08); *A23L 33/16* (2016.08); *A61K 9/0095* (2013.01); *A61K 31/05* (2013.01); *A61K 31/351* (2013.01); *A61K 31/7004* (2013.01); *A61K 31/7034* (2013.01); *A61K 31/7048* (2013.01); *A61K 33/00* (2013.01); *A61K 33/06* (2013.01); *A23V 2002/00* (2013.01); *A61K 2236/39* (2013.01)

(58) Field of Classification Search
CPC ...................................................... A61K 36/00
See application file for complete search history.

(56) References Cited

U.S. PATENT DOCUMENTS 8,841,264 B2   9/2014  Raederstorff et al.
2010/0184868 A1*  7/2010  Lopes Mas ............ A23D 7/005
                                                    514/731

FOREIGN PATENT DOCUMENTS

| EP | 1623960 A1 | 2/2006 |
| EP | 2526785 A1 | 11/2012 |
| JP | 1-101879 A | 4/1989 |
| JP | 2010-500964 A | 1/2010 |
| WO | 2005/123603 A1 | 12/2005 |
| WO | 2008/054228 A1 | 5/2008 |
| WO | 2009/132807 A1 | 11/2009 |

OTHER PUBLICATIONS

Bitler, Hydrolyzed olive vegetation water in mice has anti-inflammatory activity. The Journal of nutrition, (Jun. 2005) vol. 135, No. 6, pp. 1475-1479.*
Russo, A new membrane process for the selective fractionation and total recovery of polyphenols, water and organic substances from vegetation waters (VW). Journal of Membrane Science (2007), 288(1+2), 239-246 (Year: 2007).*

(Continued)

*Primary Examiner* — Qiuwen Mi
(74) *Attorney, Agent, or Firm* — Jeffrey N. Townes; Cozen O'Connor

(57) ABSTRACT

The present invention relates to a phytocomplex or natural concentrate rich in polyphenolic compounds, such as hydroxytyrosol and 3,4-DHPA-EDA, derived from the vegetation waters of oil-bearing olives or from olive pomace resulting from the olive milling process for use in the treatment and prevention of angiogenesis and inflammation. In particular, the angiogenesis and inflammation to which reference is made is pathologic angiogenesis and inflammation, for example that which sustains the development and spread of a tumor or angiogenesis and inflammation tied to non-tumor pathologies. The present invention further relates to a beverage comprising the polyphenol concentrate and the use thereof in the treatment and prevention of angiogenesis and inflammation.

13 Claims, 10 Drawing Sheets

(56) References Cited

OTHER PUBLICATIONS

Fernandez-Mar et al., "Bioactive compounds in wine: Resveratol, hydroxytyrosol and melatonin: A review", Food Chemistry 130: 797-813 (2012).
Garcia-Castello et al., "Recovery and concentration of polyphenols from olive mill wastewaters by integrated membrane system", Water Research 44: 3883-3892 (2010).
Kawaguchi et al., "Effects of Antioxidant Polyphenols on TNF-Alpha-Related Diseases", Current Topics in Medicinal Chemistry 11: 1767-1779 (2011).
Palmieri et al., "Effects of polyphenol extrac from olive pomace on anoxia-induced endothelial dysfunction", Microvascular Research 83: 281-289 (2012).
Petroni et al., "Inhibition of platelet aggregation and eicosanoid production by phenolic components of olive oil", Thrombosis Research 78: 151-160 (1995).
Parvaiz et al., "A: Review Therapeutic Significance of Olive *Olea europaea* L. (Oleaceae Family)", Global Journal of Pharmacology 7: 333-336 (2013).
Kiichiro Kawaguchi et al., "Effects of Antioxidant Polyphenols on TNF-Alpha-Related Diseases", Current Topics in Medicinal Chemistry, (2011), 11, 1767-1779.
M. Servili et al., "Functional Milk Beverage Fortified With Phenolic Compounds Extracted From Olive Vegetation Water, and Fermented With Functional Lactic Acid Bacteria", International Journal of Food Microbiology, 147, (2011), 45-52.

\* cited by examiner

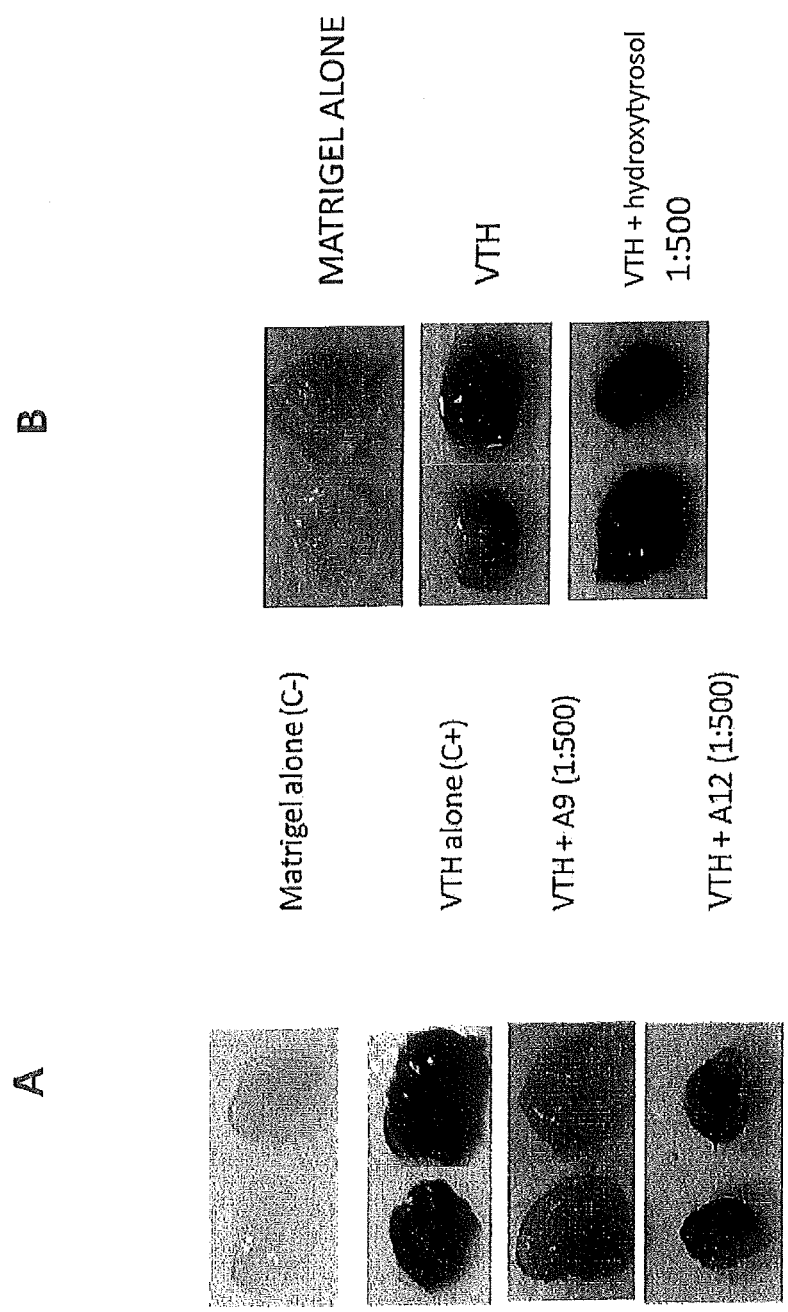

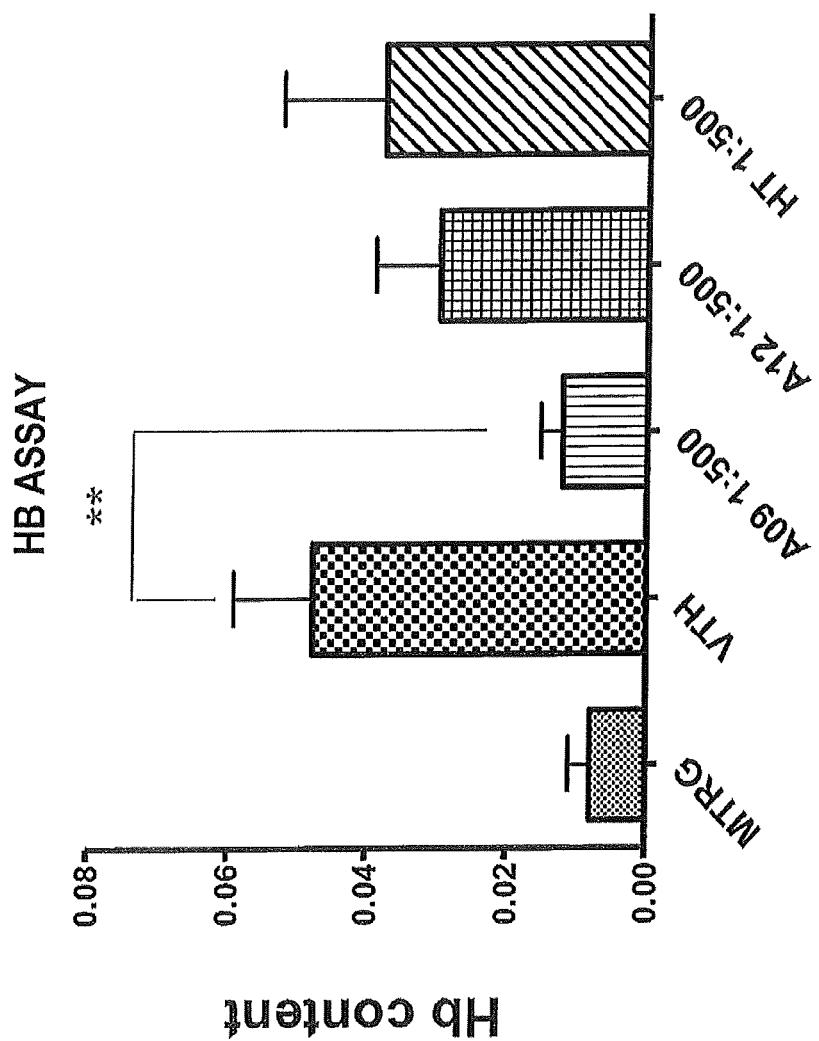

ANTIANGIOGENIC USE OF LIQUID PHYTOCOMPLEXES FROM OLIVE

CROSS-REFERENCE TO RELATED APPLICATIONS

This application is a 371 National Stage application of International PCT Application PCT/IB2014/065746, filed Oct. 31, 2014, which claims benefit of priority to Italian Patent Application No. MI2013A001814, filed Oct. 31, 2013, both of which are incorporated herein by reference in their entirety.

The present invention relates to the use of a natural phytocomplex rich in polyphenolic compounds, in particular rich in hydroxytyrosol and, 3,4-DHPA-EDA, derived from the water resulting from the pressing of oil-bearing olives (commonly known as vegetation water) or from residual olive pomace resulting from the olive milling process in the prevention and treatment of angiogenesis and/or inflammation.

In particular, the angiogenesis and inflammation to which reference is made is of a pathological type, for example that which sustains the development and spread of a tumor, or the angiogenesis and inflammation tied to non-tumor pathologies.

Angiogenesis is a physiological process which occurs during the stages of growth and development of an individual and it involves the formation of new blood vessels from those of the pre-existing vascular compartment. Angiogenesis is a process which also characterizes various pathological phenomena, including tumors.

A tumor (or neoplastic) mass can grow and develop autonomously up to a size of around 1-2 $mm^3$; however, in order to grow further, it must assure itself a vital supply of nutrients and oxygen and it therefore needs to create its own vascular compartment.

A tumor is capable secreting angiogenic factors, such as VEGF (Vascular Endothelial Growth Factor), bFGF (basic Fibroblast Growth Factor) and PDGF (Platelet-Derived Growth Factor), which are capable of promoting the development of blood vessels. The angiogenic factors secreted by the tumor activate endothelial cells, which in response begin to proliferate and secrete substances which degrade the cellular matrix and basement membranes (e.g. matrix metalloproteases-MMP) in order to migrate and invade the surrounding tissues. Subsequently, the endothelial cells organize to form tubular structures stabilized by the presence of pericytes, i.e. contractile cells which surround the newly formed blood vessels and are capable of modifying blood flow and of regulating vessel permeability.

Blood vessels deriving from tumors are irregular and are characterized by structural elements that distinguish them from "normal" vessels. For example, they are characterized by the absence of pericytes, large fenestrae and pronounced vessel dilation. These characteristics alter the permeability and pressure levels of the vessels and consequently also interfere with the delivery of anti-tumor drugs, which, instead of reaching the tumor, are dispersed in interstitial liquid and are thus unable to perform their function.

Considering the importance of angiogenesis in the processes of development, growth and metastatization of tumors, numerous studies have been conducted with the aim of identifying substances that are capable of blocking the irregular development of tumor blood vessels and are thus able to improve the delivery of drugs to the tumor site. In particular, large efforts have been made to identify molecules capable of preventing the anomalous development of blood vessels; this has led to the formulation of the concept of "angioprevention" (i.e. the prevention of tumor-related angiogenesis).

The majority of these molecules are of natural origin (or are in any case synthetic analogues). A very interesting example is molecules deriving from olive oil.

It is well known, in fact, that the incidence rates of cardiovascular pathologies and tumors are significantly lower in populations that adopt the Mediterranean diet, which is based on the consumption of olive oil.

The scientific evidence has provided a considerable incentive to the study of olive oil with the aim of defining its composition and, in particular, of identifying substances with a medical-pharmacological potential.

One characteristic of olive oil which has aroused particular interest is the high level of polyphenols contained in it. These compounds are natural antioxidants of plant origin which are capable of inhibiting the formation of free radicals.

The beneficial properties of olive oil have induced a considerable increase, above all in Italy, in olive cultivation and olive oil production. As a consequence, we have also witnessed a strong increase in by-products of olive oil production, mainly vegetation water and pomace, which are highly polluting and thus generate a considerable environmental impact.

The disposal of this material is strictly regulated in Italy on both a national and regional level and the implementation of legislation (law 574 of 11/1996) results in hefty costs for producers, who are unable to derive any advantage from these waste products, which, however, are rich in molecules with a high medical and pharmaceutical potential.

Hydroxytyrosol is the polyphenol contained in vegetation water that has been most studied. It is present in vegetation water and pomace and is formed also by hydrolysis of oleuropein, a substance that is present above all in the leaves of olive trees.

Recent research has demonstrated that hydroxytyrosol on its own has a cytoprotective effect against PC12 cells (a pheochromocytoma cell line), is anti-apoptotic when administered to U937 cells (a human myelomonocytic line) and C2C12 cells (a mouse myoblast line), inhibits breast tumor proliferation in vivo in the case of induced neoplasias, is a chemopreventive agent in studies on HL60 and HL60R tumor cell lines (a human promyelocytic leukemia line and its multi-drug resistant derivative) and is a preventive agent against premenstrual syndrome and osteoporosis.

Moreover, it has been demonstrated that in vivo administration of hydroxytyrosol (also in high concentrations) has no toxic effect.

Other research has demonstrated that when oleuropein is administered on its own, it performs an anti-microbial activity, has an anti-tumor potential in colorectal tumor cell lines, metastatic breast tumors and ER-negative cell lines and has the ability to alter cellular stability on a cytoskeletal level.

Though many studies have been undertaken on vegetation water, there is still a greatly felt need to identify new properties which can lend value to this waste product, which would otherwise be only a cost for the producer and a hazard to the environment. There is a particularly felt need to identify new nutritional and medical-pharmacological properties which may dignify this waste product.

In this regard, the Applicant has surprisingly found that vegetation water is capable of blocking/preventing, both in vitro and in vivo, angiogenesis and inflammation, in particular pathologic angiogenesis and inflammation, for example that which sustains the development and spread of a tumor, or the angiogenesis and inflammation associated with non-tumor pathologies. In particular, the Applicant has found that by concentrating, via reverse osmosis, the permeate of vegetation waters subjected to microfiltration, one obtains a phytocomplex rich in polyphenolic compounds capable of preventing and blocking angiogenesis and inflammation, in particular pathologic angiogenesis and inflammation, such as that/those associated with a tumor or that/those associated with a non-tumor pathology, in a manner that is more effective compared to what the same compounds are capable of achieving when taken individually, i.e. isolated from vegetation waters and pomace by means of purification techniques.

This effect is particularly advantageous for human health, above all in terms of angioprevention. In fact, to this end the vegetation water concentrate of the present invention, on its own or in association with further anti-tumor and anti-angiogenic and anti-inflammatory substances, can be used, for example in the form of a beverage, to treat or prevent angiogenesis and inflammation, in particular pathologic angiogenesis and inflammation associated with a tumor or pathologic angiogenesis and inflammation associated with a non-tumor disease.

BRIEF DESCRIPTION OF THE FIGURES

Further advantages of the present invention will be apparent from the detailed description that follows, which is made with the aid of the appended Figures, in which:

FIG. 9 shows the results of the macroscopic colorimetric analysis of matrigel inocula implanted beneath the skin of mice A) without treatment (matrigel alone), in the presence of VTH-VEGF,TGF,HGF (positive control C+), in the presence of VTH and a 1:500 dilution of the polyphenol concentrate of the present invention (sample A009) and the respective blank (sample A012); B) without treatment (matrigel alone), in the presence of VTH-VEGF,TGF,HGF (positive control C+), in the presence of VTH and a 1:500 dilution of purified hydroxytyrosol (HyT).

FIG. 10 shows the assay of the hemoglobin in the explanted matrigel inocula of FIG. 9.

Figure 1:
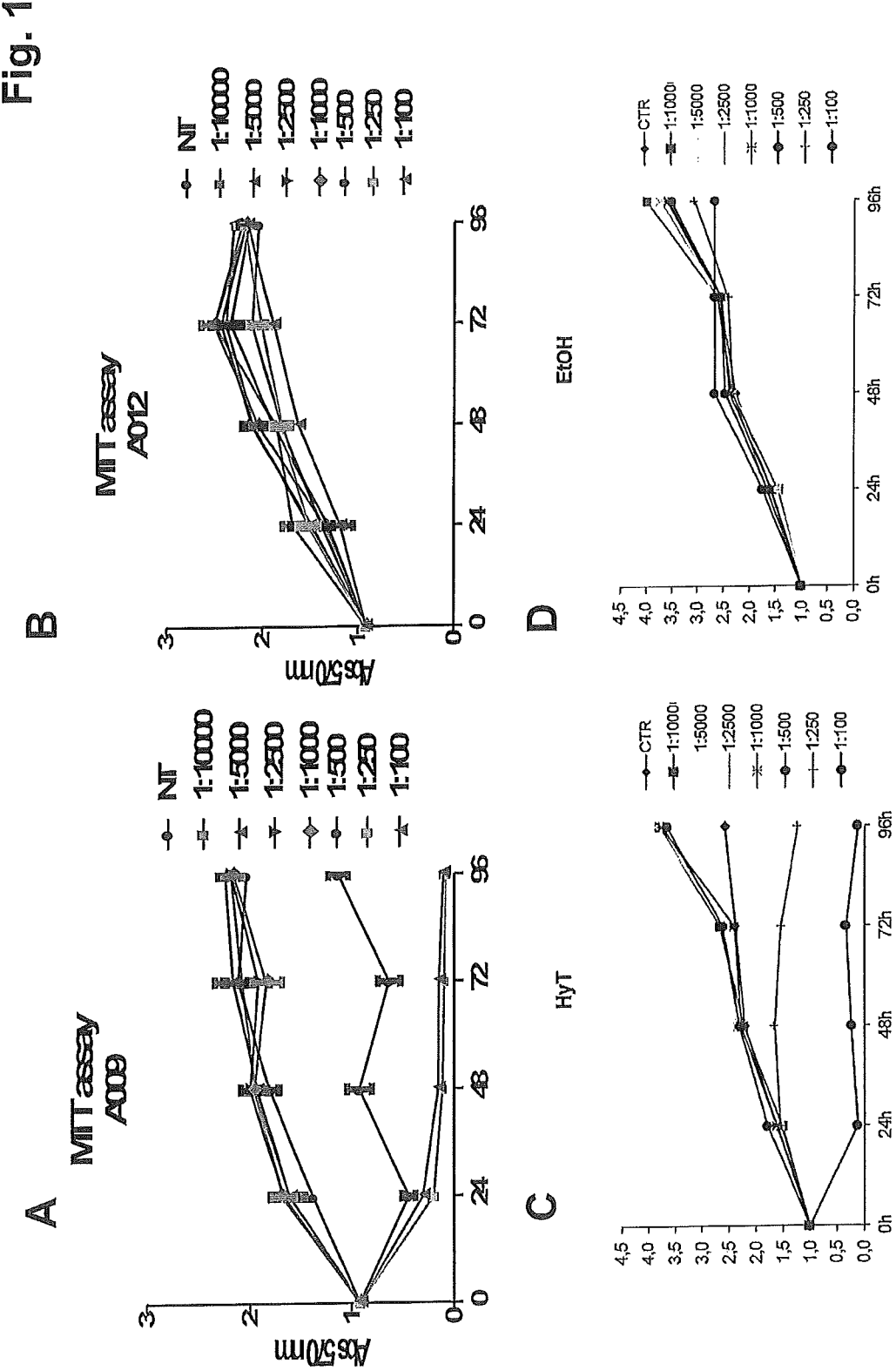
FIG. 1 shows the results of the MTT assay aimed at evaluating the proliferation of HUVE cells following treatment with progressive dilutions of: A) the polyphenol concentrate of the present invention (sample A009); B) the blank (sample A012); C) purified hydroxytyrosol (HyT); and D) the purified hydroxytyrosol blank (i.e. ethanol—EtOH).

The present invention relates to a phytocomplex or concentrate of vegetation waters and pomace comprising polyphenolic compounds, preferably hydroxytyrosol and 3,4-DHPA-EDA, for use in the treatment and prevention of angiogenesis and inflammation.

Preferably, the angiogenesis and inflammation to which reference is made is pathologic angiogenesis and inflammation, more preferably tumor-related angiogenesis and inflammation. Alternatively, the angiogenesis and inflammation may be associated not with a tumor but rather pathologies such as: rheumatic diseases, preferably rheumatoid arthritis and gout; inflammatory diseases of the colon-rectum, preferably Crohn's disease, irritable and ulcerative bowel syndrome; bronchial pathologies, preferably bronchus chronic obstructive pulmonary disease and asthma; liver diseases preferably cirrhosis and fibrosis; diseases of the prostate, preferably prostatic hyperplasia and acute/chronic prostatitis; mucositis; dermatitis or pre-neoplastic lesions, e.g. breast, uterus, lung or mouth lesions.

In fact, the concentrate of vegetation waters and/or olive pomace of the present invention surprisingly demonstrated to be particularly effective in preventing the neo-formation of tumor blood vessels (i.e. angiogenesis). These vessels have a distinctive physicochemical structure and hence biological functioning compared to normal blood vessels. They are largely fenestrated and often devoid of pericytes and for this reason have an altered vessel permeability. This structure is often at the basis of the failure or difficulties of many pharmacological treatments, because the drug is lost in interstitial spaces during delivery to the tumor through the vessels and thus either fails to reach the target or reaches it in ineffective quantities. Inhibiting the formation of this type of vessel structure clearly enables better delivery of the substances to the tumor and hence the possibility of improving the tumor treatment.

The vegetation waters preferably derive from an olive milling process with three phases (oil, vegetation waters and pomace), and two phases (oil and pomace+vegetation waters). Preferably, the vegetation waters generated by the mill can be treated with a solution with an acidic pH, preferably a pH ranging from 3 to 5, preferably 4-5, for example, through the addition of a strong acid, and with pectolytic enzymes, i.e. enzymes that hydrolyze the cellulose matrix of the olive skin.

The pomace is preferably pitted, diluted and pre-filtered. The pomace preferably has a size or cut-off ranging from 0.5 to 1 millimeter (mm), more preferably about 0.7 mm. An example of a cut-off is the one obtained with a vibration screen.

If necessary, the pitted pomace can be solubilized or dispersed in an aqueous matrix with a pH comprised from 3 to 5, preferably from 3.5 to 4. The solubilization step has the purpose of solubilizing the polyphenols which would otherwise remain trapped in the solid matrix of the olive skins. In a preferred embodiment of the invention, the concentrate of vegetation waters and/or olive pomace (hereinafter "the concentrate") further comprises: at least a further phenolic compound preferably selected from: tyrosol, chlorogenic acid, β-hydroxyverbascoside, rutin, verbascoside and luteolin; and at least one metal preferably selected from: sodium, calcium, magnesium and potassium; and at least an anion preferably selected from: chlorides, sulphates, phosphates and nitrates; and at least one glucide selected from: glucose, fructose, mannitol and sucrose.

In a further embodiment of the invention, the concentrate comprises nitrogenous substances (proteins, amino acids), preferably in an amount comprised from 15 to 60 mg/kg, more preferably from 20 to 40 mg/kg (mg of nitrogen per liter of active solution). In any case the phenolic compounds present in the concentrate in the largest amount are hydroxytyrosol and 3,4-DHPA-EDA.

Preferably, the amount of the hydroxytyrosol ranges between 1 and 10 grams per liter of vegetation waters (g/L), more preferably between 1.5 and 5 g/L, even more preferably between 2 and 3 g/L.

Preferably, the amount of 4-DHPA-EDA is comprised from 0.5 to 8 g/L, more preferably from 1 and 6 g/L, even more preferably from 1.5 to 2.5 g/L.

Preferably, the amount of tyrosol is comprised from 0.1 to 0.4 g/L, more preferably from 0.15 g/L to 0.25 g/L.

Preferably, the amount of chlorogenic acid is comprised from 0.06 to 0.24 g/L, more preferably from 0.8 to 0.16 g/L.

Preferably, the amount of p-hydroxyverbascoside is comprised from 0.3 to 1.5, more preferably from 0.5 to 1 g/L.

Preferably, the amount of rutin is comprised from 0.05 to 0.2 g/L, more preferably from 0.08 to 0.15 g/L.

Preferably, the amount of verbascoside is comprised from 0.4 to 1.7 g/L, more preferably from 0.6 to 1 g/L.

Preferably, the amount of luteolin is comprised from 0.1 to 0.5 g/L, more preferably from 0.15 to 0.28 g/L.

Preferably, the amount of sodium is comprised from 75 to 300 mg/L, more preferably from 120 to 180 mg/L.

Preferably, the amount of calcium is comprised from 5 to 10 g/L, more preferably from 2 to 5 g/L.

Preferably, the amount of magnesium is comprised from 220 to 900 mg/L, more preferably from 400 to 500 mg/L.

Preferably, the amount of potassium is comprised from 3 to 15 g/L, more preferably from 6 to 9 g/L.

Preferably, the amount of chlorides is comprised from 1.5 to 7 g/L, more preferably from 2.5 to 4.5 g/L.

Preferably, the amount of sulphates is comprised from 12 to 45 g/L, more preferably from 18 to 28 g/L.

Preferably, the amount of phosphates is comprised from 1.5 to 7 g/L, more preferably from 2.5 to 5 g/L.

Preferably, the amount of nitrates is comprised from 12 to 50 mg/L, more preferably from 18 to 30 mg/L.

Preferably, the amount of glucose is comprised from 15 to 60 g/L, more preferably from 25 to 35 g/L.

Preferably, the amount of fructose is comprised from 3.5 to 15 g/L, more preferably from 5 to 9 g/L.

Preferably, the amount of mannitol is comprised from 1 to 4 g/L, more preferably from 1.5 to 3 g/L.

Preferably, the amount of sucrose is comprised from 4 to 16 g/L, more preferably from 6 to 10 g/L.

In a preferred embodiment of the invention, the concentrate is obtained/obtainable by means of a process comprising the steps: (i) microfiltering a sample of the vegetation water and/or olive pomace so as to obtain a concentrate and a permeate of microfiltration; and (ii) concentrating by reverse osmosis the microfiltration permeate of step (i).

Preferably, the microfiltration takes places after the solubilization step as described earlier.

The microfiltration has the purpose of separating a concentrate, that is, the concentrated fraction of the content in suspension of the vegetation waters/pomace, for example micro-fragments, fibers and corpuscular material such as cells and bacteria. It is carried out under the standard conditions for this type of matrix.

In addition to the concentrate, following the microfiltration step one obtains a permeate, i.e. a clear fraction, characterized by a color that varies according to the starting material and which contains the dissolved components of the vegetation waters/pomace, e.g. proteins, sugars, salts, polyphenols, organic acids and various soluble organic molecules.

Preferably, the microfiltration is carried out with at least one and preferably two ceramic membrane(s). The membrane is preferably characterized by a tubular shape.

In a preferred embodiment, the membrane is made from aluminum oxide and zirconia.

Preferably, the membrane has the following characteristics: an outer diameter ranging from about 30 to about 40 mm, preferably about 25 mm; and a length ranging from about 500 to about 1500 mm, preferably about 1200 mm; and a series of channels with a diameter, preferably a hydraulic diameter, ranging from about 2.5 to about 5 mm, preferably about 3.5 mm; and a filtering surface ranging from about 0.15 to about 0.7 $m^2$, preferably about 0.35 $m^2$; and a molecular cut-off ranging from about 0.1 micron to about 300 kDa.

The reverse osmosis step for concentrating the permeate obtained from the microfiltration of the vegetation waters/pomace as earlier described, is carried out under the standard conditions for this type of matrix, preferably by using a polymeric membrane, more preferably made of polyamide.

In particular, the membrane has a wound spiral shape and a molecular cut-off with a high salt rejection, that is, capable of rejecting sodium chloride molecules at a percentage of 99.9%. This means that the osmosis membrane traps the molecules of biomedical interest and allows only water molecules to pass through.

Preferably, the polymeric membrane has a filtering surface which ranges from about 5 to about 15 $m^2$, and is more preferably about 7 $m^2$.

The reverse osmosis step serves to concentrate the permeate obtained from the microfiltration preferably by about 4 times; this means that from 100 L of microfiltration permeate one will obtain 25 L of concentrate. In this case the Volume Concentration Ratio (VCR) is 4, i.e. 100/25.

The VCR can change based on the starting matrix (vegetation water) and above all based on its salt content, because the process of reverse osmosis must counterbalance the osmotic pressure of the matrix that is being concentrated.

The present invention further relates to a concentrate (or phytocomplex) of vegetation waters/pomace that is obtainable/obtained with the above-described process.

The concentrate preferably has the composition earlier described in relation to the content of phenolic compounds, metals, carbohydrates, anions and nitrogen. It can be used on its own or in combination with other substances, molecules or anti-tumor and anti-angiogenic and anti-inflammatory therapies for the treatment and prevention of angiogenesis and inflammation, preferably pathologic angiogenesis and inflammation, in particular angiogenesis and inflammation associated with tumors or angiogenesis and inflammation associated with non-tumor pathologies such as: rheumatic diseases, preferably rheumatoid arthritis and gout; inflammatory diseases of the colon-rectum, preferably Crohn's disease, irritable and ulcerative bowel syndrome; bronchial pathologies, preferably bronchus chronic obstructive pulmonary disease and asthma; liver diseases preferably cirrhosis and fibrosis; diseases of the prostate, preferably prostatic hyperplasia and acute/chronic prostatitis; mucositis; dermatitis or pre-neoplastic lesions, e.g. breast, uterus, lung or mouth lesions. Preferably, the concentrate of the present invention can be used on its own or in combination with other substances/molecules, with the aim of inhibiting, preferably in a preventive manner, the formation of tumor blood vessels.

The tumors to which the present invention makes reference are preferably colorectal, breast and prostate cancer, skin cancers (melanoma and others), cancers of the pancreas, lungs, ovaries, bladder, kidneys and liver.

The inflammatory conditions associated with the angiogenesis to which the present invention makes reference are: rheumatic diseases, preferably rheumatoid arthritis and gout; inflammatory diseases of the colon-rectum, preferably Crohn's disease, irritable and ulcerative bowel syndrome; bronchial pathologies, preferably bronchus chronic obstructive pulmonary disease and asthma; liver diseases preferably cirrhosis and fibrosis; diseases of the prostate, preferably prostatic hyperplasia and acute/chronic prostatitis; mucositis; dermatitis or pre-neoplastic lesions, e.g. breast, uterus, lung or mouth lesions.

A further aspect of the present invention relates to a beverage comprising the concentrate of vegetation waters/pomace earlier described and possible excipients normally added for the production of various types of beverages.

The beverage can be based on water and fruit and milk. In the particularly preferred embodiment of the invention, the beverage is based on fruit, preferably it is a based on grape juice. Preferred in particular are grape juice and grape must, preferably from organic grapes. The beverage can optionally be lyophilized.

Alternatively, the concentrate of vegetation waters/pomace earlier described can be formulated as pills, lozenges or tablets for oral use. Practically speaking, the beverage or oral formulation can be taken as a food supplement, in particular with the aim of preventing angiogenesis and inflammation, preferably pathologic angiogenesis and inflammation, in particular that associated with a tumor or that associated with a non-tumor pathology such as: rheumatic diseases, preferably rheumatoid arthritis and gout; inflammatory diseases of the colon-rectum, preferably Crohn's disease, irritable and ulcerative bowel syndrome; bronchial pathologies, preferably bronchus chronic obstructive pulmonary disease and asthma; liver diseases preferably cirrhosis and fibrosis; diseases of the prostate, preferably prostatic hyperplasia and acute/chronic prostatitis; mucositis; dermatitis or pre-neoplastic lesions, e.g. breast, uterus, lung or mouth lesions.

Preferably, the beverage or oral formulation is taken as a food supplement with the aim of inhibiting, preferably in a preventive manner, the formation of tumor blood vessels.

Optionally, the beverage can be taken in association with anti-tumor and anti-angiogenic and anti-inflammatory substances, molecules, drugs or therapies.

A further aspect of the present invention relates to a cream, oil, ointment, mist, shampoo or gel comprising the concentrate of vegetation waters/pomace earlier described and possible excipients.

Said cream, oil, ointment or gel can be used for the treatment, preferably topical, and/or the prevention of a physiopathological condition caused by an increased and/or altered angiogenesis and by inflammation.

EXAMPLE

Production of Concentrated Polyphenols from Olive Vegetation Waters/Pomace

The entire production process is centered on the use of membrane-based tangential-flow filtration and separation technologies.

The membrane process carried out for the production of polyphenol concentrates from olive vegetation waters/pomace used only two filtration stages: microfiltration and reverse osmosis. However, depending on the product desired it is possible to complete the process with ultrafiltration and nanofiltration stages.

Microfiltration enables the separation of suspended solids, bacteria and fats, whilst reverse osmosis traps all the substances present, including ions, also monovalent ones, and allows only water to permeate.

The process was carried out starting from vegetation waters deriving from an olive milling process with three phases, but it can also be applied to wet pomace deriving from a two-phase process after a pre-treatment.

The wet pomace can be pitted, diluted and pre-filtered with a cut-off of about 0.7 mm (for example with a vibrating screen) and then treated with membrane systems; or else it can be treated in a three-phase decanter with possible dilutions and reprocessing in a three-phase decanter before being treated with membrane processes.

The microfiltration process carried out has the objective of separating the concentrated fraction of the entire contents in suspension (micro-fragments, fibers and corpuscular material such as cells and bacteria) present in the vegetation waters/pomace.

The microfiltration permeate is a clear fraction whose color differs according to the cultivar of the treated olives and which contains all of the dissolved components of the vegetation waters/pomace, e.g. proteins, sugars, salts, polyphenols, organic acids and various soluble organic molecules.

For the microfiltration, use was made of two tubular aluminum oxide ceramic membranes with a selective layer of zirconium oxide having the following characteristics: outer diameter 25 mm, length 1178 mm, 23 channels with a channel hydraulic diameter of 3.5 mm, filtering surface of 0.35 m² and molecular cut-off respectively of 0.14 micron-300 KDa.

In microfiltration, by using membranes with 23 channels having a hydraulic diameter of 3.5 mm, it is possible to concentrate the vegetation waters/pomace until obtaining a concentrated fraction with a total solids content of about 12%.

Considering the treated vegetation waters, with a content of total solids of about 7%, it was possible to concentrate by a factor of four, thus obtaining a permeate with a total solids content of 5.5% and a concentrate with a total solids content of 12.1%.

The polyphenol concentrate of the present invention was produced by concentrating the permeate obtained by microfiltering the vegetation water by reverse osmosis.

Use was made of a polymeric membrane made of polyamide with a wound spiral shape, high salt rejection and a filtering surface of 7 m², but use can also be made of membranes with low salt rejection and a minor loss of polyphenols in the permeate.

In reverse osmosis it is possible to concentrate the microfiltration permeate of the treated vegetation by a ratio of about 3.6.

Obviously, the volume concentration ratio can vary depending on the initial starting matrix and above all its salt content and hence the osmotic pressure.

Composition of the Tested Vegetation Waters

The composition of the polyphenol concentrate is indicated in Table I below:

TABLE I

| Phenolic Compounds | |
|---|---|
| Hydroxytyrosol | 2.70 g/L |
| Tyrosol | 0.20 g/L |
| Chlorogenic acid | 0.12 g/L |
| β-hydroxyverbascoside isomer 1 | 0.35 g/L |
| β-hydroxyverbascoside isomer 2 | 0.32 g/L |
| Rutin | 0.11 g/L |
| Verbascoside | 0.84 g/L |
| Luteolin-7-O-gluside | 0.22 g/L |
| 3,4-DHPEA-EDA | 1.99 g/L |

The results are expressed in g of tyrosol per L of water.
Internal standard: Syringic Acid

| Metals | |
|---|---|
| Sodium | 152 mg/L |
| Calcium | 2.95 g/L |
| Magnesium | 442 mg/L |
| Potassium | 7.6 g/L |

| Anions | |
|---|---|
| Chlorides | 3.4 g/L (expressed as NaCl) |
| Sulphates | 22.78 g/L (expressed as $K_2SO_4$) |
| Phosphates | 3.2 g/L (expressed as $PO_4^{3-}$) |
| Nitrates | 24.5 mg/L (expressed as nitric N) |

| Carbohydrates | |
|---|---|
| Glucose | 31 g/L |
| Fructose | 7 g/L |
| Mannitol | 2 g/L |
| Sucrose | 8 g/L |
| Nitrogen | 0.03% 30 mg/kg |

The substances shown in Table I are contained in the sample with the identification code A009, whereas the blank (i.e. negative control) is identified by the code A012.

The blank was obtained by batch chromatographic separation of the polyphenol concentrate with XAD 7 resin.

In detail, a volume of about 50 cc of XAD 7 resin was rinsed with distilled water, regenerated in ethanol and again rinsed with distilled water.

The resin was recovered by vacuum filtration with a 0.45 micron filter and added to about 75 ml of concentrate of vegetation waters in a beaker. The resin was left in contact with the concentrate for about 30 minutes under shaking at room temperature.

A vacuum filtration made it possible to recover the concentrate of vegetation waters treated with XAD 7 resin with an electrical conductivity of 23.4 mS/cm.

The vegetation water concentrate recovered after treatment with XAD 7 resin was again treated with XAD 7 resin, regenerated in ethanol and rinsed with distilled water.

After vacuum filtration, the third sample of the blank of vegetation water concentrate treated twice with XAD 7 resin was recovered, with an electrical conductivity of 16.92 mS/cm.

HUVECs (Human Umbelical Vein Endothelial Cells) were used as a model of the target cell of the polyphenol concentrate of the present invention, in consideration of the fact that the endothelial cell constitutes the fundamental unit of the process of angiogenesis.

The results obtained from the analyses conducted with the polyphenol concentrate were compared with those obtained when treating the HUVECs under the same conditions with hydroxytyrosol alone. Hydroxytyrosol was chosen as substance to make a comparison with as it is the polyphenol most represented in sample A009 (2.70 g/L).

The aim is to demonstrate that vegetation water (in the form of a concentrate as described), in addition to having an anti-angiogenic effect, displays a better inhibitory ability than one substance alone.

In order to assess whether the effects were actually due to the hydroxytyrosol and not to the ethanol solution in which it was dissolved, the analyses were performed using the medium containing ethanol at the same concentration in which the hydroxytyrosol is dissolved as a blank sample.

Evaluation of the Anti-Angiogenic Properties of the Vegetation Waters

The dilutions of the samples correspond to values of mg/ml and μM present in Table II below:

TABLE II

| DILUTIONS | mg/ml hydroxytyrosol | μM hydroxytyrosol |
|---|---|---|
| 1:100 | 0.0270 | 174.96 |
| 1:250 | 0.0108 | 69.984 |
| 1:500 | 0.0054 | 34.992 |
| 1:1000 | 0.0027 | 17.496 |
| 1:2500 | 0.00108 | 6.9984 |
| 1:5000 | 0.00054 | 3.4992 |
| 1:10000 | 0.00027 | 1.7496 |

Evaluation of the Anti-Proliferative Effect of the Vegetation Waters on the Endothelial Cells The effect of samples A009 and A012 on the proliferation of the human endothelial cells (HUVEC) was assessed by means of the MTT viability assay (tetrazoil salt, [3-(4,5-dimethylthiazol-2-yl)]-2,5-diphenyltetrazolium bromide). The assay is based on the ability of the MTT compound to be metabolized by a mitochondrial enzyme, succinate dehydrogenase. The reduction of the salt leads to the formation of crystals of a blue-colored product, formazan, which is insoluble in water. The viable cells, unlike the non-viable ones, reduce the salt and the amount of formazan produced is proportional to the number of cells present. The crystals formed are solubilized and the absorbance values at the wavelength of 570 nm are read via the spectrophotometer.

5000 HUVE cells were seeded in each well of a 96-well plate. In particular, the wells were coated with 1% gelatin and the assays were conducted at different treatment times (24 h, 48 h, 72 h, 96 h) and for each time different dilutions of the concentrates were tested (1:10000-1:100 intervals).

The effect on endothelial cell proliferation was evaluated for the following dilutions of concentrate: 1:10000-1:5000-1:2500-1:1000-1:500-1:250-1:100.

As can be observed from FIG. 1A, there was a significant reduction in the viability of the endothelial cells treated with sample A009, in particular, starting from the 1:1000 dilution, after 24 h of treatment.

Sample A012 (the blank) had no effect on HUVEC viability (FIG. 1B).

Hydroxytyrosol also causes a reduction in the viability of HUVE cells, in particular starting from the 1:250 dilution, after 24 h of treatment (FIG. 1C).

The medium containing ethanol, used as a control, does not produce any effect on cell viability (FIG. 1D). The experiment was conducted in duplicate and repeated twice.

It can thus be concluded, therefore, that sample A009 has a greater effect on cell viability than hydroxytyrosol.

Evaluation of Apoptosis

The induction of apoptosis (programmed cellular death) of endothelial cells treated with the concentrate was evaluated by marking with annexin V and 7-Amino-actinomycin D (7-AAD). Cytofluorimetric analysis of these markers makes it possible to distinguish, within the same cell population, the ability of a treatment to induce cell death at different stages (early, late, advanced). Annexin V is a molecule capable of binding phosphatidylserine, a glycerophospholipid of the cell membrane, normally associated with the internal cytosolic layer, which is exposed on the extracellular side as a result of cell damage. 7-AAD is a compound capable of passing through the cell membrane only in damaged cells or in apoptosis; positivity to this marker is therefore indicative of cell death and toxicity of the product.

150,000 HUVE cells were seeded in a well of 6-well plate coated with 1% gelatin. The cells were subsequently treated (for 24 h and 48 h) with different dilutions of the samples before being detached from the plate by treatment with trypsin and stained with 7-AAD and annexin V in order to evaluate the levels of apoptosis.

The endothelial cells were treated for 24 and 48 hours at different dilutions of samples A009, A012 and HyT-EtOH (range of dilutions 1:2500-1:250) and analyzed for positivity to the two markers.

Figure 2:
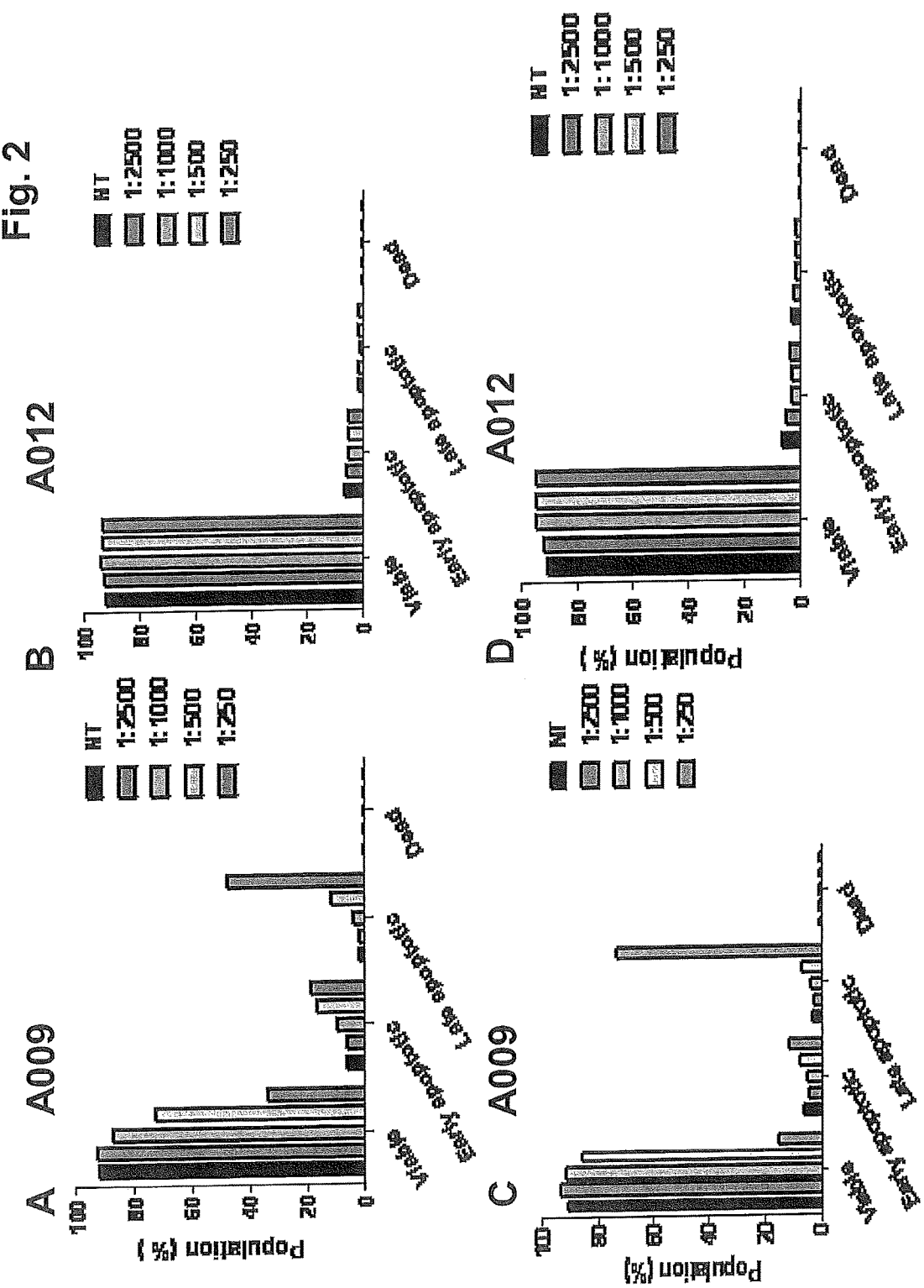
FIG. 2 shows the results of the assay on apoptosis and HUVE cell death following treatment with progressive dilutions of: A,C) the polyphenol concentrate of the present invention (sample A009); B,D the blank (sample A012) 24 and 48 hours after treatment.

As can be noted from FIGS. 2A and 2C, a 1:250 dilution of sample A009 induces the late stage of apoptosis in 50% and 75% of the endothelial cells, respectively, after 24 h and 48 h of treatment. The same dilution of sample A012 does not exert any pro-apoptotic effect (about 95% of the cells are viable).

Figure 3:
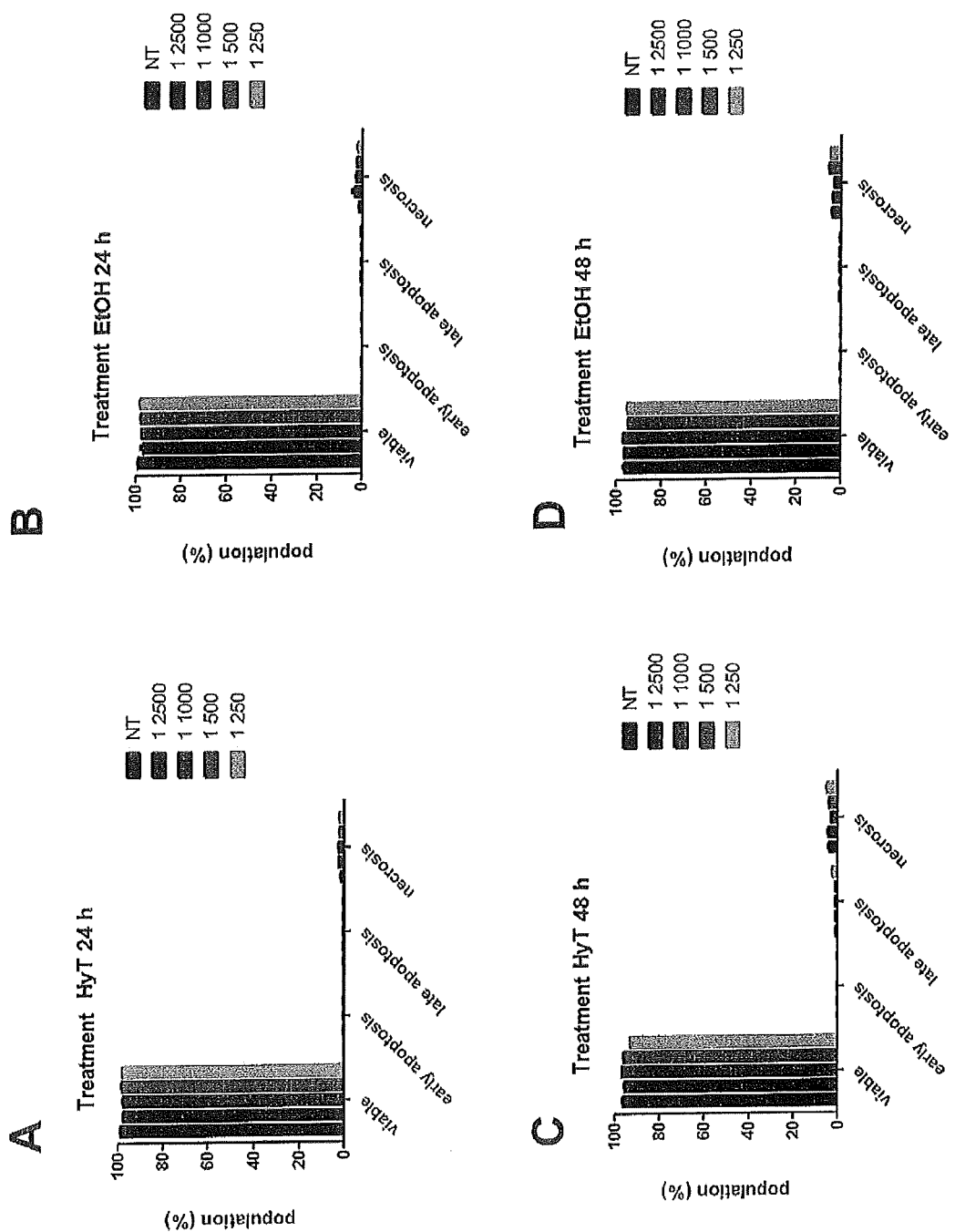
FIG. 3 shows the results of the assay on apoptosis and HUVE cell death following treatment with progressive dilutions of: A,C) purified hydroxytyrosol (HyT); B,D the purified hydroxytyrosol blank (i.e. ethanol—EtOH) 24 and 48 hours after treatment.

In contrast, the treatment with hydroxytyrosol and with the culture containing ethanol does not increase cellular necrosis (FIG. 3).

The experiment was conducted in duplicate and repeated twice.

Therefore, hydroxytyrosol displays less activity than the concentrate of the present invention.

Evaluation of the Effect of Vegetation Waters on the Morphogenesis of Endothelial Cells When they are cultured in vitro in an extracellular matrix and exposed to suitable activating stimuli, endothelial cells are capable of organizing into tubular structures which mimic the structure of the internal lumen of the vessels.

Via an assay of morphogenesis in matrigel (i.e. a polymer consisting of laminin, collagen IV, entactin, heparan sulphate proteoglycan, growth factors (e.g. PDGF, EGF, TGF-1 and MMP) it is possible to evaluate the anti-angiogenic potential of selected compounds. In order to evaluate the ability of the concentrate of the present invention to inhibit the formation of tubuli in vitro, each well of a 24-well plate was coated with 300 µL of matrigel (10 mg/mL) and, following polymerization of the matrix, 50,000 HUVE cells in 1 mL of complete medium were seeded in the polymerized matrix. The cells were pre-treated for 24 hours with different dilutions of samples A009, A012, HyT and EtOH (1:500 and 1:250).

As positive and negative controls, use was made respectively of a complete culture medium (CM) consisting of M199 medium supplemented with 10 ng/ml of aFGF (acid Fibroblastic growth factor), 10 ng/ml of bFGF (basic Fibroblastic growth factor), 10 ng/ml of EGF (Epidermal growth factor), 0.1 mg/ml of heparin, 0.10 µg/ml of hydrocortisone, 10% FBS (Fetal Bovine serum), 1% glutamin (Gln), 1% Ampicillin/Streptomycin (P/S) and the growth-factor and serum free medium M199 (SFM).

The inhibitory effect of the samples was evaluated after 6 hours of incubation at 37° C. and 5% $CO_2$, by observation under a microscope of the formation of tubular structures.

Figure 4:
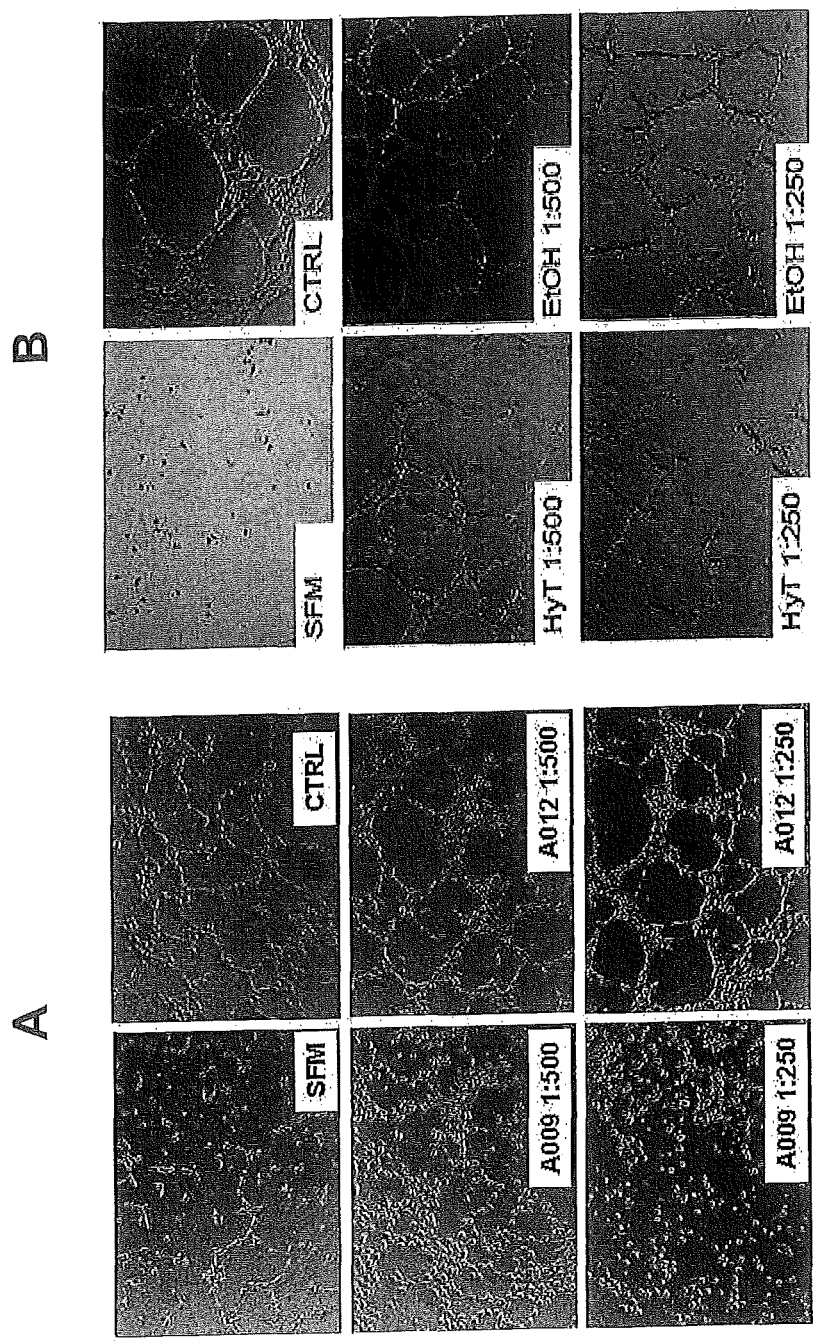
FIG. 4 shows the results of the morphogenesis assay based on an evaluation of the ability of HUVE cells to form capillary-type tubular structures in matrigel following treatment with: A) serum-free culture medium (SFM), complete culture medium (CTRL), 1:500 and 1:250 dilutions of the polyphenol concentrate of the present invention (sample A009), 1:500 and 1:250 dilutions of the blank (sample A012); B) serum-free culture medium (SFM), complete culture medium (CTRL), 1:500 and 1:250 dilutions of purified hydroxytyrosol (HyT), 1:500 and 1:250 dilutions of the purified hydroxytyrosol blank (i.e. ethanol-EtOH).

As may be observed in FIG. 4A, sample A009 is capable of interfering with the formation of stable tubular structures by the endothelial cells in a dose-dependent manner. The same dilutions of sample A012 (blank) do not exert any inhibitory effect.

Hydroxytyrosol is also capable of interfering with the formation of structures stable tubular structures by the endothelial cells in a dose-dependent manner, whereas the dilutions of ethanol (blank) exert only a slight inhibitory effect (FIG. 4B). The experiment was conducted in duplicate and repeated twice.

Therefore, hydroxytyrosol inhibits endothelial morphogenesis with a less marked effect than sample A009, i.e. than the concentrate of the present invention.

Evaluation of the Inhibitory Potential of Vegetation Waters on the Migratory Activity of Endothelial Cells Endothelial cells are characterized by the ability to migrate toward a specific site, following a chemotactic gradient. In order to evaluate the migration capacity of the HUVECs, migration assays were set up using Boyden chambers and porous filters with a cut-off of 12 µm, soaked with collagen (50 µg/mL).

The lower compartment of each chamber was loaded with 210 µL of CM containing 10 ng/mL αFGF, 10 ng/ml bFGF. 10 ng/mL EGF, 0.1 mg/mL heparin, 0.10 µg/mL hydrocortisone, 10% FBS, 1% Gln, 1% P/S or growth-factor and serum free medium M199 (SFM).

50000 HUVE cells pre-treated for 24 hours with diverse dilutions (1:2500, 1:1000, 1:500 and 1:250) of concentrate, of the blank, of hydroxytyrosol or of the medium containing ethanol were seeded in the upper compartment of the chamber, in 500 µL of serum free medium.

The cells were incubated at 37° C., 5% $CO_2$ for 6 h.

At the end of the assay, the filters were mechanically cleaned so as to eliminate the non-migrating cells on the upper side; they were then fixed in absolute ethanol for 5 minutes, and subsequently rehydrated and marked with the viability stain DAPI. The cells present on each filter were counted under a fluorescence microscope. In particular, 5 optical fields per filter were analyzed in a random manner.

Figure 5:
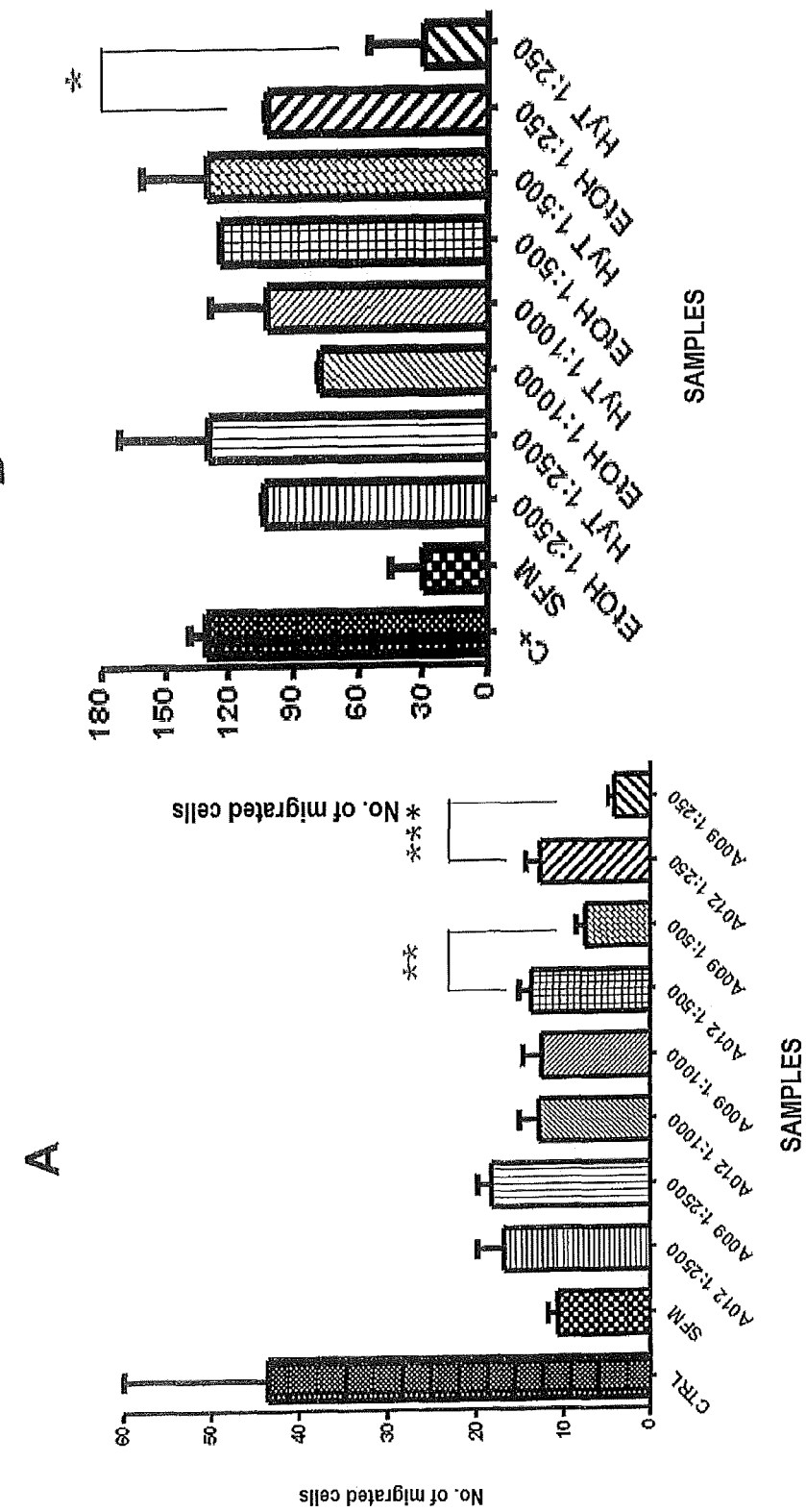
FIG. 5 shows the results of the chemotaxis assay on HUVE cells following treatment with: A) complete culture medium (CTRL), serum-free culture medium (SFM), progressive dilutions of the polyphenol concentrate of the present invention (sample A009), the blank (sample A012); B) complete culture medium (C+), serum-free culture medium (SFM), progressive dilutions of purified hydroxytyrosol (HyT) and of the purified hydroxytyrosol blank (i.e. ethanol-EtOH).

As shown in FIG. 5A, the concentrate of the present invention (sample A009) is capable of interfering with the migratory capacity of the endothelial cells to a statistically significant degree at the 1:500 and 1:250 dilutions (p-value=0.0057 and p-value=0.0003, respectively), whereas sample A012 (blank) does not interfere with the migratory capacity of the same.

Hydroxytyrosol reduces the migratory capacity of the endothelial cells compared to the medium with ethanol used at the 1:250 dilution with a p-value=0.0302 (FIG. 5B). It can also be observed that at higher dilutions of hydroxytyrosol the endothelial cells show an increase in migratory capacity, whereas the concentrate of the present invention inhibits it. The experiment was conducted in duplicate and repeated twice.

Therefore, hydroxytyrosol used as a single substance displays a lower ability to interfere with endothelial migration, i.e. it is not effective.

Evaluation of the Inhibitory Potential of Vegetation Waters on the Invasive Activity of the Endothelial Cells Once recruited in situ, endothelial cells have the ability to invade the surrounding tissues, producing factors capable of degrading the extracellular matrix, which constitutes a physical barrier to their actual migration to the chemotactic site.

The invasion assay was set up using Boyden chambers and porous filters with a cut-off of 12 µm, coated with matrigel (1 mg/mL).

210 µL of complete culture medium (CM) containing 10 ng/mL aFGF, 10 ng/ml bFGF, 10 ng/mL EGF, 0.1 mg/mL heparin, 0.10 µg/mL hydrocortisone, 10% FBS, 1% Gln, 1% P/S or 210 µL of growth-factor and serum free medium M199 (SFM) were poured into the lower compartment of each chamber.

50000 HUVE cells resuspended in 500 µL of SFM and pre-treated for 24 hours with different dilutions (1:2500, 1:1000, 1:500 and 1:250) of concentrate, of the blank, of hydroxytyrosol and of the solution without hydroxytyrosol were incubated at 37° C., 5% $CO_2$ for 24 h.

At the end of the assay, the filters were mechanically cleaned so as to eliminate the cells present on the upper side which had not penetrated beyond the matrix. The filters containing the cells that had invaded the matrigel were fixed in absolute ethanol for 5 minutes, and then rehydrated and marked with the viability stain DAPI. The cells present on each filter were counted under a fluorescence microscope; 5 optical fields per filter, selected in a random manner, were subjected to analysis.

Figure 6:
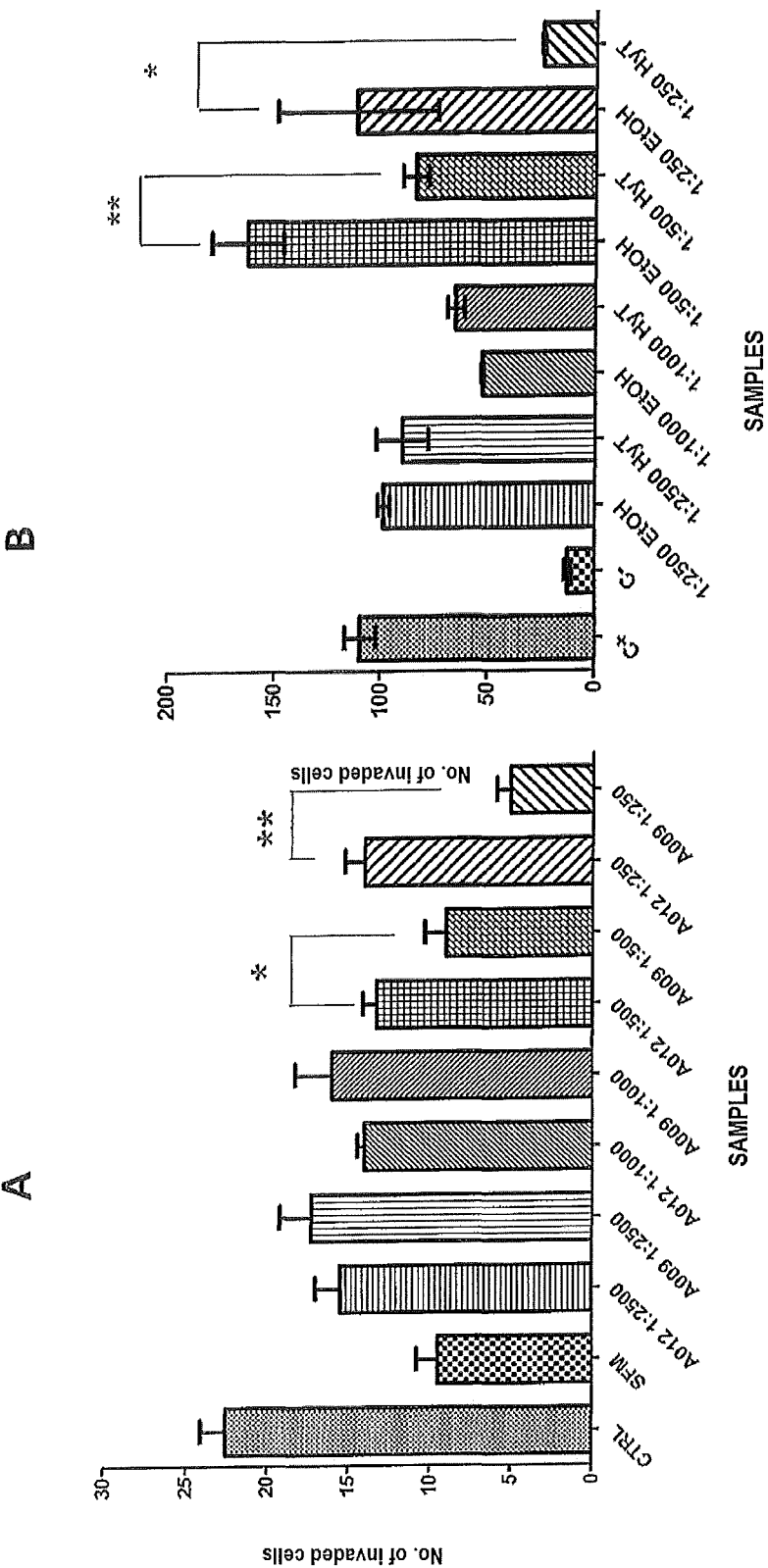
FIG. 6 shows the results of the chemoinvasion assay on the HUVE cells following treatment with: A) complete culture medium (CTRL), serum-free culture medium (SFM), progressive dilutions of the polyphenol concentrate of the present invention (sample A009), the blank (sample A012); B) complete culture medium (C+), serum-free culture medium (C−), progressive dilutions of purified hydroxytyrosol (HyT) and of the purified hydroxytyrosol blank (i.e. ethanol-EtOH).

The results shown in FIG. 6A demonstrate that sample A009 (i.e. the concentrate of the present invention) is capable of interfering with the invasive capacity of the endothelial cells to a statistically significant degree at the 1:500 and 1:250 dilutions (p-value=0.0335 and p-value=0.0011, respectively), whereas sample A012 (blank) does not influence the invasive capacity of the same.

As shown in FIG. 6B, hydroxytyrosol reduces the invasive capacity of the endothelial cells compared to the medium with ethanol used at the 1:500 and 1:250 dilutions with a p-value=0.0016 and p-value=0.0159.

Hydroxytyrosol has better effectiveness considering longer times, since it inhibits cell invasion, but not migration.

The concentrate of the present invention functions effectively against both migration and invasion.

Evaluation of the Protective Role Against Damage Due to Oxidative Stress by the Vegetation Waters after Treatment with $H_2O_2$ Reactive Oxygen Species (ROS) represent one of the main mechanisms of cellular damage and play a fundamental role in the inflammation process and, as a consequence, in the angiogenesis correlated with inflammation. An assessment was thus made of the antioxidant potential vis-à-vis HUVE cells subjected to treatment with the vegetation water concentrates after treatment with $H_2O_2$, by marking with DCFH-DA (2',7'-dichlorfluorescein-diacetate).

DCFH-DA is a substance capable of revealing the concentration of intracellular $H_2O_2$ and can be detected by cytofluorimetry.

150,000 HUVE cells were seeded in complete medium in each well of a 6-well plate coated with 1% gelatin. The cells were subsequently trypsinized and resuspended in complete M199 medium with $H_2O_2$ at a concentration of 250 µM. The cells were then placed in an incubator at 37° C. and 5% $CO_2$, in the dark, for 15 minutes. The cells were subsequently washed with DPBS and the supernatant was then eliminated by 5 minutes' centrifugation at 1200 rpm. Finally, the cells were resuspended in DPBS containing 10 µM of DCFH-DA and $H_2O_2$ (positive control) or dilutions of the concentrates (A009 and A012), of hydroxytyrosol or of solvent free of hydroxytyrosol. The cells were incubated at 37° C. in an atmosphere containing 5% CO2 for 45 minutes in the dark. Finally, the results were read using a FACSCanto.

Figure 7:
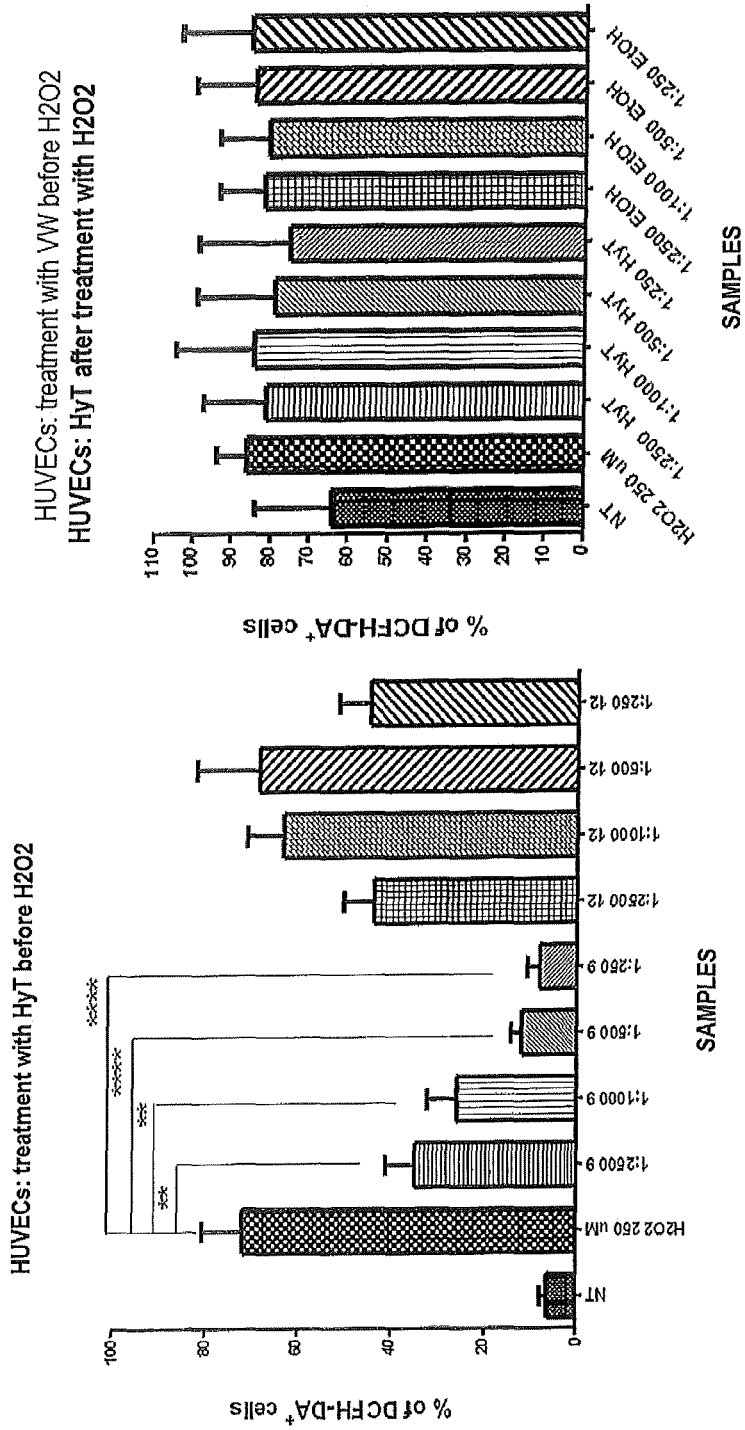
FIG. 7 shows the results for the oxidative stress (measured as % of DCFH-DA$^+$ cells) affecting HUVE cells treated with $H_2O_2$ prior to treatment with A) progressive dilutions of the polyphenol concentrate of the present invention (sample A009) and respective blank (sample A012); B) progressive dilutions of purified hydroxytyrosol (HyT) and the respective blank (i.e. ethanol-EtOH).

The results summarized in FIG. 7A demonstrate that sample A009 (the concentrate of the present invention) is capable of exerting a protective effect in a dose-dependent manner and to a highly significant degree: p-value 1:2500=0.0310, p-value 1:1000=0.0001, p-value 1:500=0.0001, p-value 1:250<0.0001.

Hydroxytyrosol exerts an antioxidant effect (FIG. 7B), whereas the medium in which the ethanol is dissolved possesses no antioxidant effect.

The results demonstrate that the concentrate of the present invention is capable of exerting a more significant antioxidant effect. The p-values for hydroxytyrosol are in fact lower: p-value 1:2500=0.0115, p-value 1:1000=0.0062, p-value 1:500=0.0082 and p-value 1:250=0.0223.

The experiment was conducted in duplicate and repeated twice.

Evaluation of the Protective Role Against Damage Due to Oxidative Stress by the Vegetation Waters Before Treatment with $H_2O_2$ 150,000 HUVE cells were seeded in complete medium in each well of a 6-well plate coated with 1% gelatin. The cells were subsequently trypsinized and resuspended in complete M199 medium and the vegetation water concentrates (A009 and A012), the hydroxytyrosol or medium containing ethanol at the standard dilutions.

The cells were then placed in an incubator at 37° C. and 5% $CO_2$, in the dark, for 30 minutes. After washing with DPBS, the cells were resuspended in DPBS with 10 µM of DCFH-DA and $H_2O_2$ both in the positive control and in the samples under analysis. The cells were placed in an incubator at 37° C. and 5% $CO_2$ for 45 minutes in the dark. Finally, the results were read using a FACSCanto.

Figure 8:
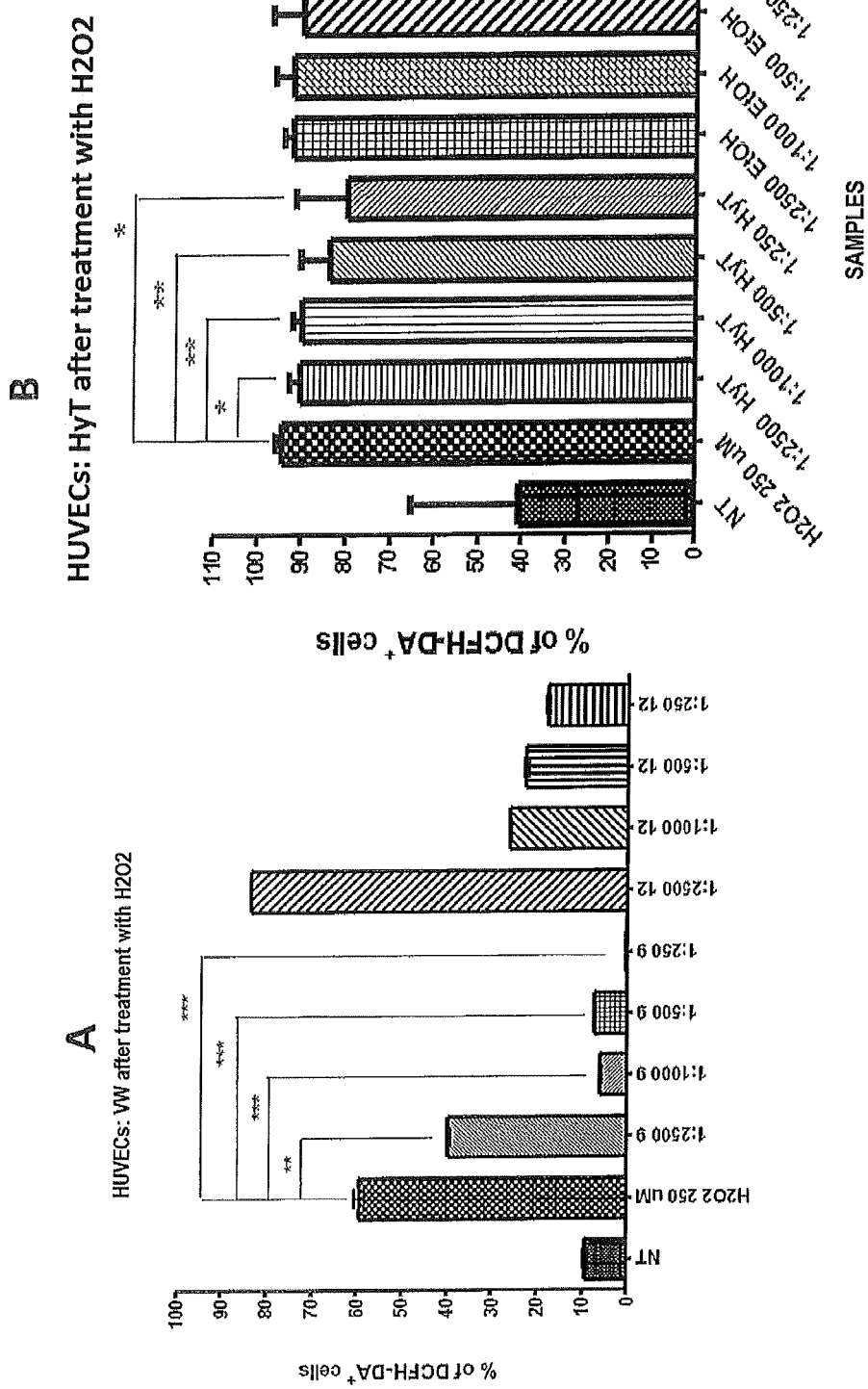
FIG. 8 shows the results for the oxidative stress (measured as % of DCFH-DA$^+$ cells) affecting HUVE cells treated with $H_2O_2$ following pre-treatment with A) progressive dilutions of the polyphenol concentrate of the present invention (sample A009) and respective blank (sample A012); B) progressive dilutions of purified hydroxytyrosol (HyT) and the respective blank (i.e. ethanol-EtOH).

In FIG. 8A it may be observed that sample A009 exerts a protective effect in a dose-dependent manner, whilst it can be observed that the production of ROS remains high in the samples treated with the blank (A012). The reduction in the production of ROS is highly significant in the case of sample A009: p-value 1:2500=0.0056, p-value 1:1000=0.0015, p-value 1:500<0.0001 and p-value 1:250<0.0001.

The results shown in FIG. 8B demonstrate that hydroxytyrosol has no significant antioxidant effect if used after induction of oxidation by $H_2O_2$. Furthermore, it is possible to observe that the solvent without hydroxytyrosol produces no significant effect on the cells, as occurs in the case of pre-treatment with $H_2O_2$.

The experiment was conducted in duplicate and repeated twice.

In conclusion, besides having a lower antioxidant power than the concentrate of the present invention, hydroxytyrosol does not maintain this potential if used in a pre-treatment after induction of oxidation.

Evaluation of the Anti-Angiogenic Potential of Vegetation Waters in a Mouse Model The ability of the vegetation water concentrate to inhibit blood vessel formation in vivo was evaluated by means of the matrigel sponge assay as described by Albini et al. in "Angiogenic potential in vivo by Kaposi's sarcoma cell-free supernatants and HIV-1 tat product: inhibition of KS-like lesions by tissue inhibitor of metalloproteinase-2 (AIDS, 1994)".

Specifically, 8-week-old male mice of the strain c57/BL6 were used as an animal model. Matrigel pellets were injected subcutaneously into the mice, in association with sample A009, at different dilutions, or the corresponding blank (A012). Matrigel appears in liquid form at a temperature of 4° C., and rapidly polymerizes at room temperature; this property is exploited to simulate a subcutaneous tumor which secretes pro-angiogenic substances. In this experiment, the matrigel in liquid form was associated with a mixture called VTH containing all of the factors necessary for the process of angiogenesis, and consisting of VEGF (100 ng/µl), TNF α (1.2 ng/µl) and heparin (25 U/ml).

VTH is considered a positive control, since VEGF represents the main growth factor for endothelial cells, TNFα constitutes a cytokine that is essential for recruiting the inflammatory cellular component and heparin serves to retain the blood that forms in the pellet as a result of the recruitment and activation of the endothelium. Once injected subcutaneously in the animal's flanks, matrigel polymerizes rapidly and releases the factors contained in it. They act as a chemoattractant for the endothelium and inflammatory cells which, once they have infiltrated the matrigel, remain trapped and become activated in the "microenvironment" formed by the matrix. For the assay in question, 3 mice were used for each condition. The conditions used were: 1) matrigel alone (negative control), 2) matrigel and VTH (positive control), 3) matrigel with VTH in combination with 2 dilutions of the vegetation water concentrate (1:500 and 1:250), both for the sample under analysis and the blank sample. Moreover, the same dilutions were tested for hydroxytyrosol.

The matrigel pellets were injected on day 0; on day 4 the mice were sacrificed and the pellets were removed. The explanted pellets were weighed and placed in 300 µl of PBS, and then divided into two parts: half was used for the assay of hemoglobin, which is an indicator of angiogenesis (in the presence of blood in the pellet as a result of the recruitment of the endothelial cell and its activation), whereas the other half was embedded in OCT in order to carry out immuno-histochemical staining to evaluate the endothelial and inflammatory component.

For the purpose of quantifying the hemoglobin, the pellets were mechanically disintegrated, centrifuged at 4° C. for 12 minutes at 13000 g and the supernatant was removed.

200 µl of supernatant was then placed in an Eppendorf tube, where 800 µl of Drabkin solution were added. This substance binds to hemoglobin to form crystals which precipitate, thus enabling absorbance to be read by means of a spectrophotometer (540 nm): the hemoglobin concentration is directly proportional to the number of crystals formed and the recorded absorbance. The quantification of hemoglobin relied on the following mathematical model:

$$HB = (\text{absorbance at 540 nm/weight in mg of the pellet}) \times 100$$

In FIG. 9A it is possible to observe that the staining is proportional to the infiltration of the endothelium and consequent presence of blood.

In FIG. 9B it is possible to observe that the staining of the pellets of the 1:500 treatment with hydroxytyrosol is greater than that of the positive control.

FIG. 10 shows the data related to quantification of the hemoglobin content of the pellets. It can be noted that the hemoglobin concentration decreases in the pellets associated with the concentrate of the present invention (A009), to a statistically significant degree (p-value=0.0058) compared to the pellets associated with sample A012 (blank) and to hydroxytyrosol.

In conclusion, the experimental results reported above clearly indicate that the polyphenol concentrate obtained from vegetation waters (sample A009) is endowed with anti-angiogenic activity. In fact, the concentrate of the present invention inhibits the viability and increases the apoptosis of endothelial cells. Moreover, it also prevents the migration and invasion of the synthetic matrices used to simulate the extracellular matrix. Finally, by treating the HUVECs with the concentrate of the present invention it is also possible to observe the inhibition of the formation of the tubular structures of the vasculature.

In addition to the in vitro results, the anti-angiogenic potential of the concentrate of the present invention was clearly demonstrated also in a physiological system.

All of the experiments were conducted comparing the concentrate with the same concentrate purified of the polyphenols (blank sample) so as to be able to affirm that the observed effects were due to the molecules of interest and not to other factors that might have interfered with the experiments.

Furthermore, hydroxytyrosol was also tested on its own and the results of all the tests carried out demonstrated that it is less effective and active than the concentrate of the present invention.

Therefore, the results of the experiments set forth above demonstrate that the polyphenol concentrate obtained by subjecting the microfiltration permeate of vegetation waters to reverse osmosis possesses anti-angiogenic properties.

In particular, the concentrate has an improved anti-angiogenic effect compared to hydroxytyrosol alone, which represents the main polyphenolic compound contained in the vegetation waters.

The invention claimed is:

1. A method of using a composition comprising a concentrate of vegetation waters and/or olive pomace comprising hydroxytyrosol and 3,4-dihydroxyphenolethanol-elenolic acid di-aldehyde (3,4-DHPA-EDA) to treat angiogenesis, comprising the step of administering the composition to a patient in need thereof, wherein the composition treats angiogenesis.

2. The method according to claim 1, wherein the concentrate further comprises: at least one phenolic compound selected from: tyrosol, chlorogenic acid, β-hydroxyverbascoside, rutin, verbascoside, and luteolin; and/or at least one metal selected from: sodium, calcium, magnesium and potassium; and/or at least one anion selected from: chlorides, sulphates, phosphates and nitrates; and/or at least one carbohydrate selected from: glucose, fructose, mannitol and sucrose; and/or nitrogen.

3. The method of claim 1, wherein the composition is a beverage.

4. The method according to claim 3, wherein the angiogenesis is a pathologic tumor or non-tumor angiogenesis.

5. The method according to claim 4, wherein the angiogenesis is a non-tumor angiogenesis selected from rheumatic diseases; inflammatory diseases of the colon-rectum; bronchial pathologies; liver diseases; diseases of the prostate; mucositis; dermatitis or pre-neoplastic lesions.

6. The method according to claim 1, wherein the angiogenesis is a pathologic tumor or non-tumor angiogenesis.

7. The method according to claim 6, wherein the angiogenesis is a non-tumor angiogenesis selected from rheumatic diseases; inflammatory diseases of the colon-rectum; bronchial pathologies; liver diseases; diseases of the prostate; mucositis; dermatitis or pre-neoplastic lesions.

8. A method of using a concentrate of vegetation waters and/or olive pomace, to treat angiogenesis, comprising the step of administering said concentrate to a patient in need thereof,
wherein the concentrate treats angiogenesis, and
wherein the method is prepared by a process for producing the concentrate of vegetation water and/or olive pomace comprising the steps of:
(i) microfiltering a sample of vegetation water and/or olive pomace with a membrane made of aluminum oxide and zirconia to obtain the concentrate and a permeate of microfiltration; and
(ii) concentrating by reverse osmosis the microfiltration permeate of step (i).

9. The method according to claim 8, wherein the angiogenesis is a pathologic tumor or non-tumor angiogenesis.

10. The method according to claim 9, wherein the angiogenesis is a non-tumor angiogenesis selected from rheumatic diseases; inflammatory diseases of the colon-rectum; bronchial pathologies; liver diseases; diseases of the prostate; mucositis; dermatitis or pre-neoplastic lesions.

11. The method according to claim 8, wherein the concentrate further comprises: at least one phenolic compound selected from: tyrosol, chlorogenic acid, β-hydroxyverbascoside, rutin, verbascoside, and luteolin; and/or at least one metal selected from: sodium, calcium, magnesium and potassium; and/or at least an anion selected from: chlorides, sulphates, phosphates and nitrates; and/or at least one carbohydrate selected from: glucose, fructose, mannitol and sucrose; and/or nitrogen.

12. A method of using a composition comprising a concentrate of vegetation waters and/or olive pomace comprising hydroxytyrosol and 3,4-dihydroxyphenolethanol-elenolic acid di-aldehyde (3,4-DHPA-EDA) to inhibit tumor blood vessel formation, comprising the step of administering the composition to a patient in need thereof, wherein the composition inhibits tumor blood vessel formation.

13. The method according to claim 12, wherein the concentrate further comprises: at least one phenolic compound selected from: tyrosol, chlorogenic acid, β-hydroxyverbascoside, rutin, verbascoside, and luteolin; and/or at least one metal selected from: sodium, calcium, magnesium and potassium; and/or at least an anion selected from: chlorides, sulphates, phosphates and nitrates; and/or at least one carbohydrate selected from: glucose, fructose, mannitol and sucrose; and/or nitrogen.

* * * * *